US00PP22219P3

(12) United States Plant Patent
Orton et al.

(10) Patent No.: US PP22,219 P3
(45) Date of Patent: Nov. 1, 2011

(54) INTERSPECIFIC HYBRID DOGWOOD TREE DESIGNATED 'KF 111-1'

(50) Latin Name: *(Cornus kousa×C. florida 'Sweetwater')×C kousa*
Varietal Denomination: KF 111-1

(75) Inventors: Elwin R. Orton, Hillsborough, NJ (US); David A. Gant, Wall Township, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 11 days.

(21) Appl. No.: 12/589,649

(22) Filed: Oct. 27, 2009

(65) Prior Publication Data

US 2011/0099674 P1 Apr. 28, 2011

(51) Int. Cl.
*A01H 5/00* (2006.01)

(52) U.S. Cl. ..... Plt./220

(58) Field of Classification Search ..... Plt./220
See application file for complete search history.

*Primary Examiner* — June Hwu
*Assistant Examiner* — Louanne Krawczewicz Myers
(74) *Attorney, Agent, or Firm* — James A. Lucas; Driggs, Hogg, Daugherty & Del Zoppo Co., LPA

(57) ABSTRACT

An advanced generation interspecific hybrid of *Cornus kousa* and *C. florida* that is distinguished by its exceptionally high vigor, attractive foliage, very floriferous display of white floral bracts, high level of winter hardiness, tolerance of drought and shade, and high resistance to the incitants of Powdery Mildew and Dogwood Anthracnose.

5 Drawing Sheets

BACKGROUND OF THE INVENTION

This new cultivar is a product of a longstanding detailed program of interspecific hybridization and selection of dogwoods, in this instance a cross of an $F_1$ interspecific hybrid of *Cornus kousa×C. florida* 'Sweetwater' backcrossed to an unrelated *C. kousa*. The progeny were carefully retained and characteristics analyzed for their differences and outstanding value as potential commercial varieties or cultivars.

The particular seedling hereof were selected from certain progeny grown in a cultivated area and, as a result, have in turn been asexually reproduced by grafting, usually by T-budding or chip-budding. It can also be propagated by softwood stem cuttings. The reproduction and actual growth and selection of the new cultivar took place in the vicinity of New Brunswick, N.J. and has been found to be distinctive as to its winter-hardiness in that area, USDA Plant Hardiness Map Zone 6a. This new cultivar is stable and reproduces true to type in successive generations of asexual reproduction.

As will be understood from the detailed description of the invention that appears hereinafter, the new cultivar is in fact outstanding and readily identified as such. With the foregoing in mind, the description that follows will be understood as clearly defining the new cultivar, the desirable characteristics of which are the result of such a program as has been heretofore suggested.

SUMMARY OF THE INVENTION

The variety was originated or discovered in a cultivated area on a horticulture farm near New Brunswick, N.J. from a cross in June, 1989 between an $F_1$ interspecific hybrid (seed parent) resulting from a controlled cross of *Cornus kousa×C. florida* 'Sweetwater', and an unnamed *C. kousa* (pollen parent). The complete parentage of the claimed plant can be summed as follows:

(*Cornus kousa×C. florida* 'Sweetwater')×*C. kousa*

None of the antecedent parent plants are patented.

The seedling which became this new cultivar emerged in a seed flat on Mar. 8, 1991 and, subsequently, was transplanted to progressively larger plant-growing containers as follows: one gallon, Mar. 21, 1991; two-gallon, May 22, 1991; 3-gallon, Jul. 25, 1991; 4.5 gallon, Jun. 16, 1992; 7 gallon, Apr. 13, 1993; 15 gallon, Aug. 6, 1993. On Oct. 10, 1994, the plant was field planted at a research site in Millstone, N.J. where it has been thoroughly tested to the present time. It has also been propagated in Tennessee and Oregon. To the best of our knowledge, this new variety is the first reported advanced generation interspecific hybrid of these two species. Furthermore, its fruit has ornamental value as contrasted with other hybrids of these species. The fall foliage of the plant is quite spectacular.

BRIEF DESCRIPTION OF THE DRAWINGS

This new variety of dogwood is illustrated by the accompanying photographic drawings, depicting the plant by the best possible color representation using color photography. All color references below are measured against The Royal Horticultural Society Colour Chart (R.H.S.). Copyright 1966 Colors of foliage, floral bracts, and other plant parts may vary from year to year depending on horticultural practices, light conditions, air temperature, soil fertility, etc.

BOTANICAL DESCRIPTION OF THE INVENTION

Figure 1:
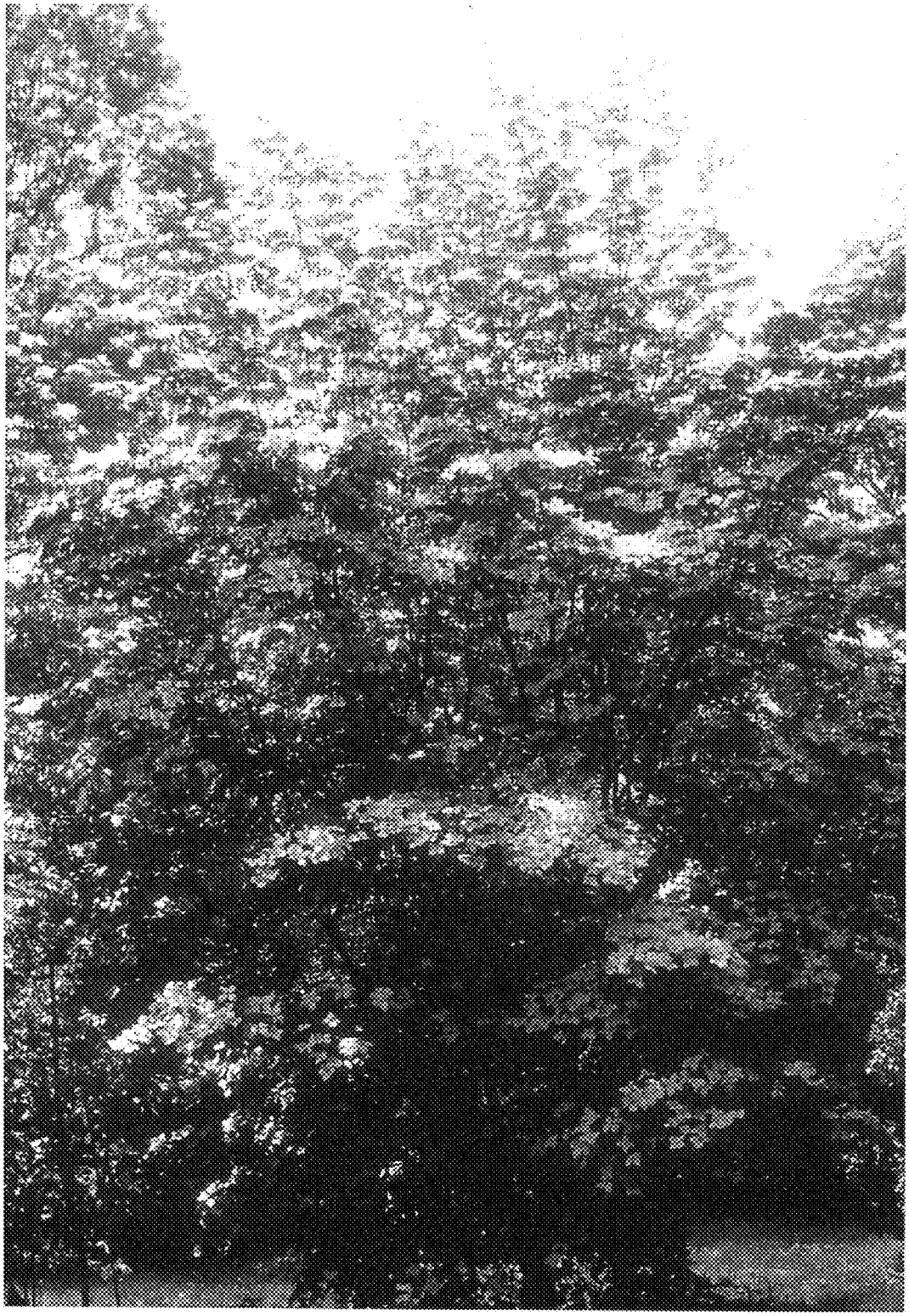
FIG. 1 shows the original seedling tree of the present invention after 17 years.
Figure 2:
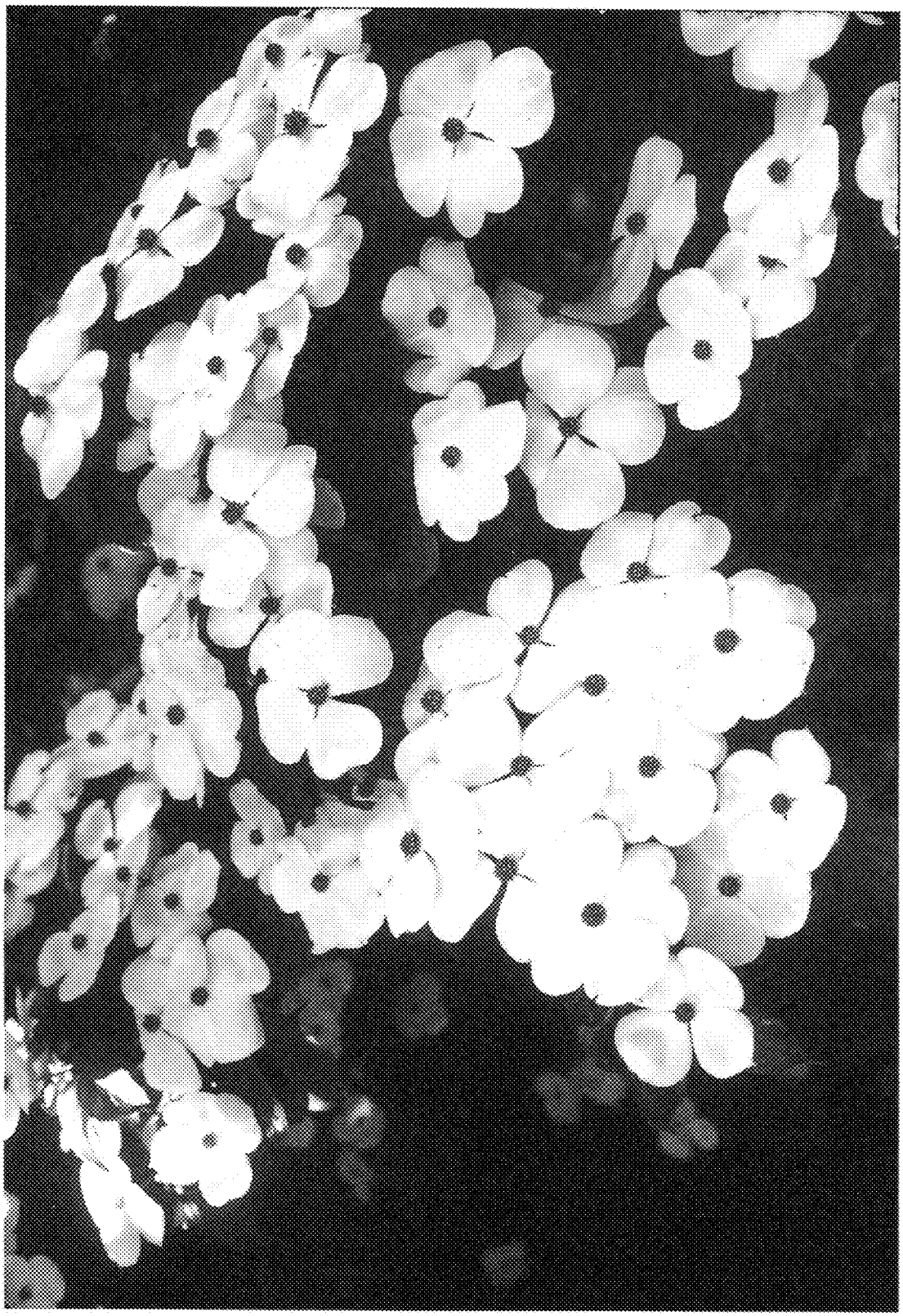
FIG. 2 shows leaf and floral display of original seedling at the peak of floral display.
Figure 3:
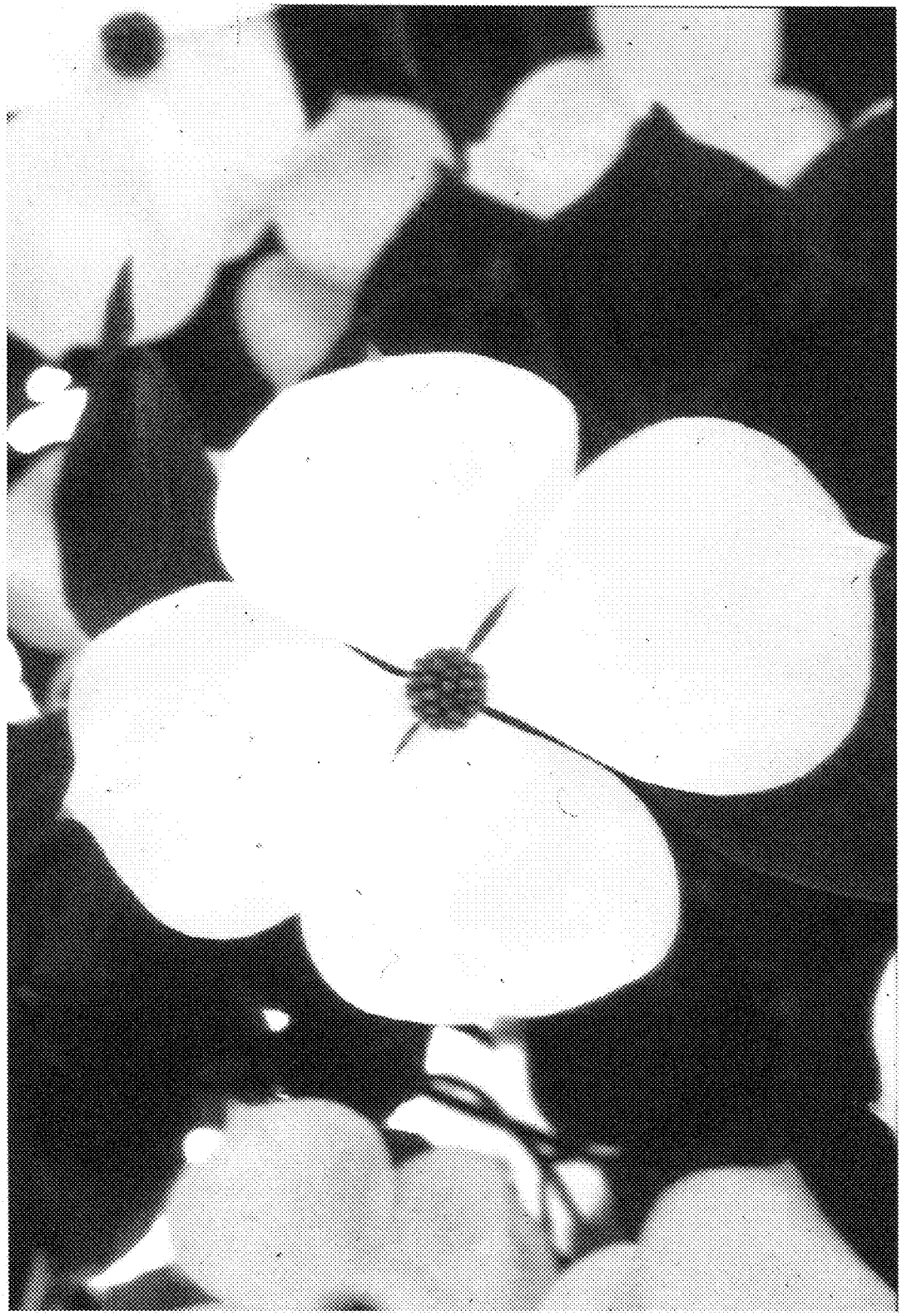
FIG. 3 shows a single flower head in bloom.
Figure 4:
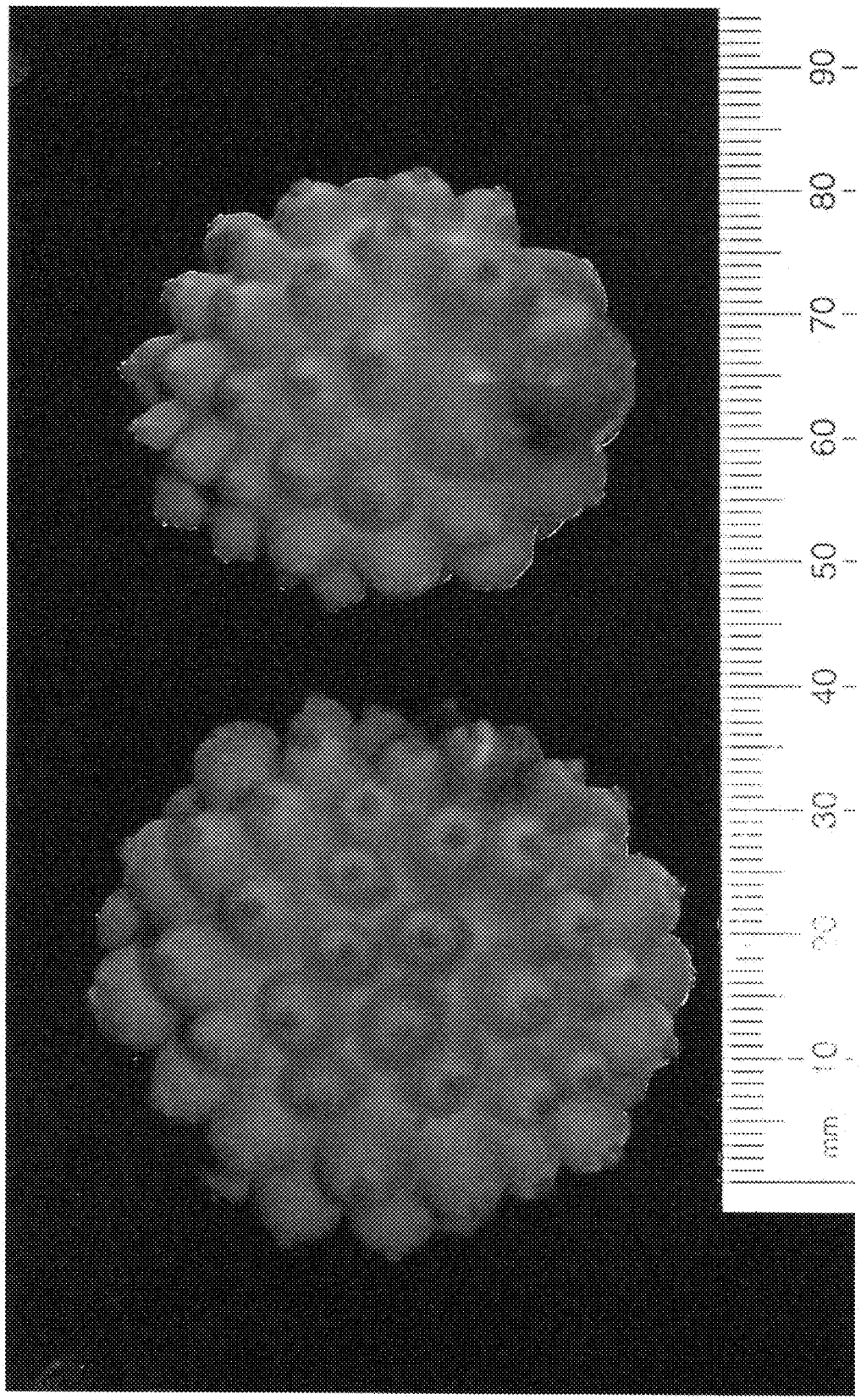
FIG. 4 shows two fruits which illustrate the difference between a fruit containing no drupelets with a viable developing seed, and a fruit showing the enlarged fleshy area around a drupelet containing a seed.
Figure 5:
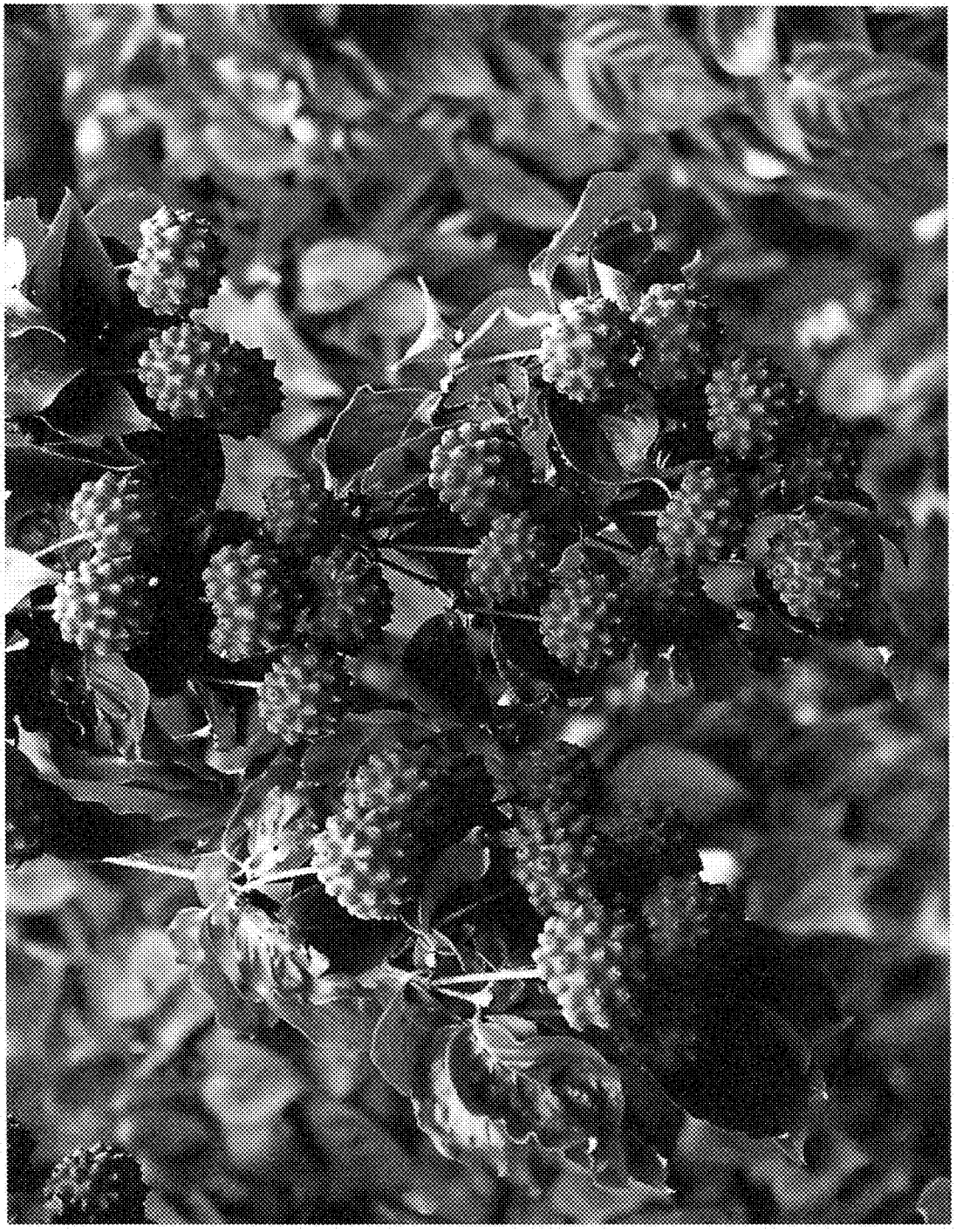
FIG. 5 shows the foliage and fruit (most contain no viable seed) on several branches.

Botanical designation: (*Cornus kousa×C. florida* 'Sweetwater')×*C kousa*.

Variety denomination: 'KF 111-1'

PLANT

Form: Tree.

Growth habit: Tree branched low to ground with upright branches which spread outward after about 10-15 years.

*Height.*—7.62 meters at 19 years.

*Width.*—6.71 meters at 19 years.

The ornamental value of the fruit display of 'KF 111-1' is a characteristic that distinguished it from all of the current F1 interspecific hybrids (our Stellar® series of dogwood plants being the the only $F_1$ interspecific hybrids of *C. kousa*×*C. florida*) since plants of those hybrids are completely sterile and the fruit they produce are of no ornamental value.

Plant vigor: Plants of this new variety are very vigorous. The original seedling was 2.29 meters in height and well branched at the end of the first growing season. Budded liners propagated and grown in Tennessee typically reach a height of 0.91 to 1.22 meters in one year, with a few reaching a height of 1.52 meters. One-year liners are stout and well branched. The plants are much more vigorous than any cultivars of *C. florida* or *C. kousa* known to the inventors and are more vigorous than plants of any of the seven cultivars of the Stellar® series of hybrid dogwood ($F_1$ generation interspecific hybrids of *C. kousa*×*C. florida*).

Cold hardiness: Original seedling has suffered no winter injury during the 16 years it has been observed in the field at Millstone, N.J. in USDA Plant Hardiness Map Zone 6a (−5° F. to −10° F.).

Resistance to insects and disease: No insect or disease problems were observed during the 16 years the original seedling of the cultivar 'KF 111-1' has been tested in the field.

Trunk: Circumference of the crown of the original seedling at the soil level was 0.95 meters after 19 growing seasons. Moderate to heavy exfoliating bark on basal 1.52 m of trunk.

Color: 197D Greyed-Green Group in areas between lenticels and 197A to 197B Greyed-Green group in areas of numerous lenticels.

*Underside of exfoliating bark.*—165B Greyed-Orange Group.

*Surface under exfoliated bark.*—165D and 165A Greyed-Orange Group.

Lenticels: Approximately 16/cm$^2$ on basal 1.83 meters of trunk. Shape somewhat oval with a length of 1.24 mm and a wish of 0.88 mm, raised edge and depressed center, coloration RHS 201A grey group, based on n=10 observations.

Texture: Sandpaper rough.

Branches:

*Color.*—197B Greyed-Green Group.

*Texture.*—Fairly smooth with many small bumps (lenticels).

*Crotch angle.*—Large, basal branches — 70°-85°; smaller branches — 25°-40°.

*Internode length.*—13.2 cm (n=25); range 8.9-20.3 cm. Wherein n is the number of observations.

The two major branches originating on the central trunk at a height of 20 cm and 31 cm above soil level constitute the structure of the original seedling. The two side branches are slightly obovate in shape and measure 16 cm and 19 cm in diameter at 19 years. The shape of the small lateral branches of the basal 2.5 meters of the tree are markedly obovate in shape, giving them a muscular appearance near the point of attachment, the stems becoming increasing rounded in form as they lengthen.

FOLIAGE

Leaf arrangement: Opposite

Leaf size: Lamina

| Year | n | Average length (cm) | Range in length (cm) | Average width (cm) | Range in width (cm) |
|---|---|---|---|---|---|
| 2005 | 10 | 14.25 | 11.1-15.5 | 9.38 | 8.3-10.8 |
| 2009 | 10 | 12.8 | 11.6-16.2 | 7.20 | 5.9- 9.1 |

*Tip.*—Apiculate.

*Shape.*—Ovate.

*Base.*—Attenuate.

*Margin.*—Mildly crenulate.

Texture: Lamina flat and quite smooth on abaxial surface in spite of a moderate number of small white hairs. Adaxial surface has a prominent midrib and four, sometimes five, pairs of moderately prominent pairs of lateral veins. Small, short hairs cover the entire surface, which is downy due to many longer white hairs along the edges of the midrib and the lateral veins.

Other features: Prominent dense tufts of long, light brown almost submicroscopic hairs at the axils of the lateral veins and the midrib.

Quantity: Many, densely foliaged.

Mature foliage color:

*Adaxial.*—Closest to, but darker than 137A Green Group with a narrow line (144B Yellow-Green Group) on the midrib from the tip of the petiole to the base of the uppermost pair of lateral veins.

*Abaxial.*—Closest to 138D Green Group with a narrow line (145C Yellow-Green Group) on the midrib.

Autumn foliage color: Attractive. Some leaves remain green (141A Green Group and 143A Green Group) but most of the leaves are about 50% green with mottled areas of 166A Greyed-Orange Group, 145A Yellow-Green Group, 14 B Yellow-Orange Group, 15A Yellow-Orange Group and 187A Greyed-Purple Group.

*Petiole.*—Length: average 11 mm (range 6-15) n=20. Width: average 1.7 mm (range 1-2) n=20. Color: 145A Yellow-Green Group. Other feature: dense mat of short hairs (200B Brown Group) at inner base (point of attachment).

Disease resistance: Asexually propagated plants of his hybrid variety have been tested in New Brunswick, N.J.; Millstone, N.J.; Winchester, Tenn.; and Boring, Oreg. with no evidence of susceptibility to the incitants of Powdery Mildew or Dogwood Anthracnose.

Shade tolerance: Plants of this new hybrid have proven to grow well under conditions of 60%-65% shade, in addition to thriving under complete exposure to full sunlight.

INFLORESCENCE

Location where observations were made: Research field in Millstone, N.J.

Type of inflorescence: Flowerhead. Dense, rounded mound.

Number of true flowers per flower head:

TABLE 1

| Number of true flowers per flower head: | | | |
|---|---|---|---|
| Year | n | average | range |
| 2003 | 125 | 51.6 | 40-63 |
| 2004 | 10 | 53.6 | 50-58 |
| 2005 | 20 | 48.9 | 40-55 |
| 2006 | 33 | 51.3 | 43-61 |
| 2008 | 27 | 50.6 | 42-62 |
| 2009 | 25 | 48.0 | 43-57 |

The average number of true flowers per flower head of this new cultivar is quite uniform from year to year.

TABLE 2

| Peduncle: size and color: | | | | |
|---|---|---|---|---|
| | | Average | | |
| Year | n | length (cm) | width (mm) | Color |
| 2005 | 15 | 7.1 | 2.1 | 145A Yellow-Green Group |
| 2006 | 23 | 9.5 | 2.0 | " |
| 2009 | 25 | 7.2 | 1.9 | " |

FLORAL BRACTS

Number: Four, in two opposing pairs:

TABLE 3

| Size of floral bracts: | | | | | |
|---|---|---|---|---|---|
| | Length of lower bracts (cm) | | Width of lower bracts (cm) | Involucral spread of lower bracts (cm) | |
| Year | n | Average | Average | n | Average |
| 2005 | 30 | 5.28 | 6.11 | 15 | 10.75 |
| 2006 | 48 | 5.88 | 5.95 | 24 | 11.95 |
| | Length of upper bracts (cm) | | Width of upper bracts (cm) | Involucral spread of upper bracts (cm) | |
| Year | n | Average | Average | n | Average |
| 2005 | 30 | 5.89 | 5.43 | 15 | 11.99 |
| 2006 | 48 | 6.30 | 5.09 | 24 | 12.80 |

The size of the floral bracts will vary due to environment factors such as temperature, sunlight, rainfall and fertilizer practices. However, the lower, floral bracts are always shorter and wider than the upper floral bracts.

Color: At start of floral display (early to mid-May):

*Adaxial surface.*—Closest to 150D Yellow-Green Group and slightly lighter toward the tip; fine line of 51A Red Group along the margins and tips of the bracts.

*Abaxial surface.*—Closest to 150D Yellow-Green Group with 155D White Group toward tip and base; trace of 51A Red Group at margins and tip. One week after the start of the floral period:

*Adaxial surface.*—Closest to 4D Yellow-Group with trace of 52B Red Group along margins and tip.

*Abaxial surface.*—Closest to 155B White Group with trace of 52B Red Group along margins and tip.

Shape: Broadly rounded

Apex: Abruptly acute

Base: Broadly acuminate

Bract stalk length: 3-4 mm

Bract stalk width: 5-6 mm

Bract margins: Entire.

Flower description: Very floriferous. Single flowers arranged in compact, dense heads subtended by the large floral bracts. No observed fragrance. Flowers not persistent.

Flowering habit: Anthesis of the tiny, relatively inconspicuous true flowers generally commences 4-6 days following the onset of the ornamental display of the large floral bracts which generally occurs in central New Jersey in early to mid-May and continues approximately for 2.5 to 3 weeks or more depending on the prevailing weather conditions. Floral development is asynchronous within the inflorescence.

REPRODUCTIVE ORGANS

Stamens: Number per flower—4.

*Filament size.*—4-5 mm long and 0.25-0.30 mm wide.

*Anther size.*—Approximately 1.0 mm long and 0.56 mm wide.

*Color.*—Pre-anthesis: closest to 12A Yellow Group. Post-anthesis: closest to 153D Yellow-Orange Group. Pollen color — closest to 20A Yellow-Orange Group. Pistil: Number — 1.

*Style length.*—Approximately 1.5 mm long and 0.5 mm diameter.

*Stigma height.*—Approximately 0.25 mm.

*Color of style.*—145A Yellow-Green Group.

*Color of stigma.*—Closest to 153C Yellow-Green Group.

FRUIT

Flower head with mature fruit: Fruits are many two-celled, one seeded drupelets (ovary inferior), fused at the base in areas surrounding a drupelet containing a developing seed, and forming a multiple fruit. A low percentage of the drupelets contain a developing seed, whereas all of the known $F_1$ interspecific hybrids of *C. kousa*×*C. florida* in commerce are extremely cross-sterile. However, a multiple fruit of 'KF 111-1' does not develop into a smooth, rounded, strawberry-like fruit similar to that of *C. kousa* unless there are a number of drupelets that contain a developing seed which stimulates basal fusion and enlargement of surrounding drupelets. Thus, the external surface of the fruit is rough, albeit rounded, due to the small protruding drupelets that do not contain a developing seed. An aggregate fruit of *C. kousa* is plump and rounded with a smooth surface even in the absence of any developing seed. The multiple fruit of the 'KF 111-1' hybrid matures in mid-September in the vicinity of central New Jersey.

Size of fruit: Height in cms: 2.7 cm (n=43); width in cms: 3.1 cm (n=43).

Color: Large fused ovaries near a seed — 46A and 46B Red Group. Smaller, protruding ovaries without a seed: 45A Red Group.

Seed: Round and narrowly tapered to four sections at proximal end.

Color: 161C-161D Greyed-Yellow Group.

Size: Average length — 7.24 mm (n=15). Average width — 4.62 mm (n=15).

Texture: Rough.

What is claimed is:

1. A new and distinct cultivar of dogwood tree, substantially as herein shown and described, comprising an advanced generation interspecific hybrid of *Cornus kousa*×*C. florida* 'Sweetwater' with an unrelated plant of *C. kousa*.

* * * * *